(12) United States Patent
Kuan et al.

(10) Patent No.: US 9,310,356 B2
(45) Date of Patent: Apr. 12, 2016

(54) CALLIGRAPHY PAPER-BASED BIOMEDICAL TESTING SHEET AND ITS MANUFACTURING METHOD

(71) Applicant: National Tsing Hua University, Hsin Chu (TW)

(72) Inventors: Chen-Meng Kuan, Hengshan Township, Hsinchu County (TW); Chao-Min Cheng, New Taipei (TW); Kuan-Hung Chen, Kaohsiung (TW)

(73) Assignee: NATIONAL TSING HUA UNIVERSITY, Hsin Chu (TW)

( * ) Notice: Subject to any disclaimer, the term of this patent is extended or adjusted under 35 U.S.C. 154(b) by 0 days.

(21) Appl. No.: 14/270,685

(22) Filed: May 6, 2014

(65) Prior Publication Data

US 2014/0356252 A1 Dec. 4, 2014

(30) Foreign Application Priority Data

May 28, 2013 (TW) .............................. 102118839 A

(51) Int. Cl.
*G01N 33/52* (2006.01)
*G01N 33/66* (2006.01)

(52) U.S. Cl.
CPC .............. *G01N 33/521* (2013.01); *G01N 33/66* (2013.01)

(58) Field of Classification Search
CPC .................................................... B01L 3/5088
See application file for complete search history.

(56) References Cited

U.S. PATENT DOCUMENTS

| 5,210,021 A | * | 5/1993 | Goodwin, Jr. ................... 435/29 |
| 5,405,894 A | * | 4/1995 | Best .............................. 524/166 |
| 6,027,513 A | * | 2/2000 | Massana Florensa ........ 606/134 |
| 2009/0298191 A1 | * | 12/2009 | Whitesides et al. .......... 436/164 |

FOREIGN PATENT DOCUMENTS

TW 200846661 12/2008

OTHER PUBLICATIONS

Carrilho E—Understanding wax-printing a simple micropatterning process for paper-based microfluidics—Anal Chem.

* cited by examiner

*Primary Examiner* — Jill Warden
*Assistant Examiner* — Matthew Krcha
(74) *Attorney, Agent, or Firm* — Foster Pepper PLLC; Richard A. Koske

(57) ABSTRACT

A biomedical testing sheet comprises: a substrate with calligraphy paper material, wherein the substrate comprises a wax pattern layer, which is a part of a surface of the substrate coated by a waxy material, and penetrated and diffused by the waxy material, and the wax pattern layer comprises one or more carrying units for carrying one or more droplets of liquids to be measured. The lotus effect substantially prevents diffusion of the liquids and reagents on the carrying units, and reduces the required amount of liquids to be measured and the amount of agent.

14 Claims, 5 Drawing Sheets

CALLIGRAPHY PAPER-BASED BIOMEDICAL TESTING SHEET AND ITS MANUFACTURING METHOD

FIELD OF THE INVENTION

The present invention is related to a testing sheet, specifically, a biomedical testing sheet.

DESCRIPTION OF THE PRIOR ART

Health has always been an important issue in human life, and, with the economic growth and the development of civilization, the spread of relevant diseases has increased in the modern time. The concept of disease prevention has long been accepted by the public, and the early testing methods are developed for this purpose. Conventional tests for many diseases are expensive and require manpower and specialized equipment. Thus, only large hospitals and institutions can provide such testing services.

Disease testing methods include invasive methods and in vitro methods. In vitro testing methods are becoming popular because they are safer, more convenient, and more effective compared to the complicated testing services provided by the large hospitals.

For example, diabetes is a global human health threat not only because of the disease itself, but also because of the accompanying symptoms. This threat inspired the development of the relevant testing device. Currently, many manufacturers focus on electrochemical testing, which requires complex testing processes and instruments. Another drawback is that most instruments are electrical, which not only consumes energy, but also the poor popularity for the poor countries or regions without abundant resources.

Nitrite is an odorless, slightly salty, white and pale yellow crystalline or granular powder that is widely used by the modern food industry as a food additive in many meat products. National standards stipulate that nitrite in processed meat shall not exceed 30 mg per kilogram. Nitrite is highly toxic, and the toxic dose is about 0.2 to 0.5 grams. Large doses can cause poisoning and even death within 1-3 hours after eating. However, death can occur from 10 minutes to 20 hours after eating.

After the nitrite is digested by the human body, the methemoglobin of the blood malfunctions and causes tissue hypoxia and then cyanosis poisoning. Symptoms include bruising on the lips, tongue, or fingers. In severe cases, bruising occurs on the conjunctiva or skin of the face or body, and the patient experiences nausea, vomiting, cramps, diarrhea, or even coma, convulsions, incontinence, or death due to respiratory failure. Compared to the chemical toxicity of the nitrite itself, the carcinogenic nitrosamine resulted from the nitrite and primary amine is much more dangerous. Epidemiological surveys show that many human cancers such as stomach, esophagus, liver, colon and bladder cancers may be related to nitrosamines.

Even so, most countries approve the use of nitrite in meat as a color fixative and preservative because it gives meat a beautiful and bright red color. It also has antiseptic effects that inhibit anaerobic clostridium bacteria, especially the clostridium botulinum, to prevent meat poisoning. Since no better alternatives are available, nitrite is widely used in the processed meat.

Therefore, based on the above-mentioned medical or food safety reasons, a simple and inexpensive biomedical testing sheets for testing glucose concentrations in human urine or nitrite concentrations in food is required.

SUMMARY OF THE INVENTION

The invention aims to solve the above problems. The Lotus effect is used to prevent diffusion of the liquids to be measured and diffusion of the reagents on the carrying units, and thus reduces the required amount of the liquids and reagents without outflowing due to the lack of adhesion. Thus, the biomedical testing sheet of the invention is stable and easy to operate. Notably, unlike the conventional OR Unlike the conventional biomedical testing sheet, the calligraphy paper material and waxy materials used in the invention are very inexpensive, and the technique to coat the waxy material on the calligraphy paper material is also simple and inexpensive. In addition to its low cost, its advantages include high stability and ease of handling. The biomedical testing sheet of the invention is also applicable for cell testing, antibody testing or other biomedical testing.

An aspect of the invention provides a biomedical testing sheet comprising: a substrate with calligraphy paper material, wherein the substrate comprises a wax pattern layer, which is a part of a surface of the substrate coated by a waxy material, and penetrated and diffused by the waxy material, and the wax pattern layer comprises one or more carrying units for carrying one or more droplets of liquids to be measured. Alternatively, the calligraphy paper material is polyvinyl chloride.

Alternatively, one or more carrying units can be rectangular, one or more carrying units can form a matrix, and one or more carrying units can be separated by a distance. Further, the one or more carrying units are the same size.

Another aspect of the invention provides a method for manufacturing a biomedical testing sheet, comprising steps of: coating a waxy material on a surface of a substrate; heat treating the waxy material to make the waxy material penetrate the substrate to form a wax pattern layer, wherein calligraphy paper is the preferred material of the substrate.

Alternatively, the wax pattern layer can be formed into one or more carrying units, which are rectangular. Alternatively, one or more carrying units can be formed into a matrix. Alternatively, one or more carrying units can be separated by a distance.

BRIEF DESCRIPTION OF THE DRAWINGS

The primitive objectives and advantages of the present invention will become apparent upon reading the following description and upon reference to the accompanying drawings in which.

DESCRIPTION OF THE PREFERRED EMBODIMENT

For a clear understanding of the manner in which the above-recited details and other advantages and objects according to the invention are obtained, the invention is described in detail with reference to the best-contemplated mode and specific embodiments thereof. The following description of the invention is intended to illustrate the general principles of the invention and should not be taken in a limiting sense; it is intended to illustrate various embodiments of the invention. As such, the specific modifications discussed are not to be construed as limitations on the scope of the invention.

It will be apparent to one skilled in the art that various equivalents, changes, and modifications may be made without departing from the scope of the invention, and it is understood that such equivalent embodiments are to be included herein. The terminology used in the description presented below is intended to be interpreted in its broadest reasonable manner, even though it is being used in conjunction with a detailed description of certain specific embodiments of the invention. Certain terms may even be emphasized below; however, any terminology intended to be interpreted in any restricted manner will be overtly and specifically defined as such in this detailed description section. Where the context permits, singular or plural terms may also include the plural or singular term, respectively. Moreover, unless the word "or" is expressly limited to mean only a single item exclusive from the other items in a list of two or more items, then the use of "or" in such a list is to be interpreted as including (a) any single item in the list, (b) all of the items in the list, or (c) any combination of items in the list.

Figure 1:
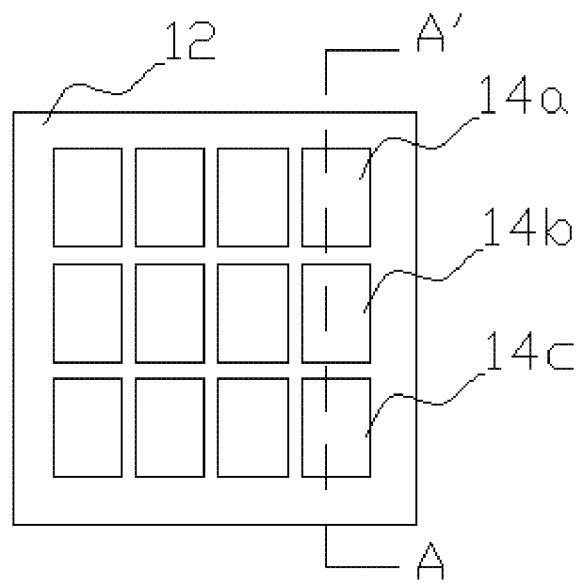
FIG. 1 is a top view of the biomedical testing sheet according to one embodiment of the invention.

FIG. 1 is a top view of the biomedical testing sheet according to an embodiment of the invention with the carrying units to carry droplets, for example, carrying units 14a, 14b, and 14c.

Figure 2:
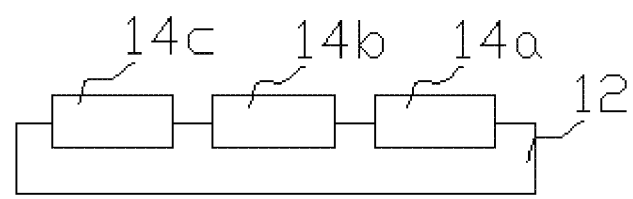
FIG. 2 is a sectional view along the line AA' of the biomedical testing sheet in FIG. 1.

FIG. 2 is a sectional view along the line AA' of the biomedical testing sheet in FIG. 1. The biomedical testing sheet 10 of the invention comprises: a substrate 12 having a calligraphy paper material, such as polyvinyl chloride. Wherein the substrate layer 12 comprises a wax pattern layer, comprising: carrying unit 14a, carrying unit 14b, carrying unit 14c, etc., for carrying one or more droplets to be measured. Further, the wax pattern layer is a part of a surface of the substrate that is coated with a waxy material, and penetrated and diffused by the waxy material.

By referring to FIG. 1, the biomedical testing sheet 10 has one or more carrying units (14a, 14b, 14c), which are rectangular. The one or more carrying units (14a, 14b, 14c) form a matrix. For example, the biomedical testing sheet 10 shown in FIG. 1 comprises a 4×3 matrix of carrying units. The one or more carrying units (14a, 14b, 14c) are separated by a distance, and the one or more carrying units (14a, 14b, 14c) are the same size.

By referring to FIG. 2, the invention provides a method for manufacturing the biomedical testing sheet 10, comprising steps of: (1) coating a waxy material on the surface of substrate 12 with the calligraphy paper material; (2) heat treating the waxy material so that the waxy material penetrates substrate 12 to form a wax pattern layer. FIG. 2 shows that the wax pattern layer can be formed into one or more carrying units, including: carrying units 14a, 14b, 14c, and etc. Alternatively, the one or more carrying units (14a, 14b, 14c) can be formed into the rectangular carrying units, and the one or more carrying units (14a, 14b, 14c) can form a matrix. Alternatively, the one or more carrying units (14a, 14b, 14c) can be formed separated by a distance.

Figure 3:
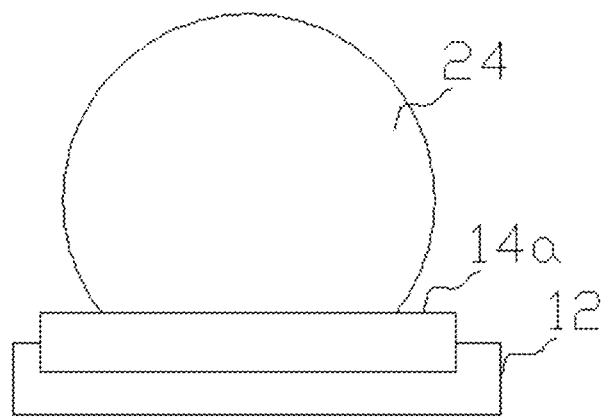
FIG. 3 illustrates a sectional view of a glycerin droplet, which is dropping on the biomedical testing sheet of the invention.

FIG. 3 illustrates a sectional view of a glycerin droplet 24, which is dropped onto the biomedical testing sheet of the invention. As shown, the contact angle that the glycerin droplet 24 contacts the surface of the carrying unit 14a of the biomedical testing sheet shows that the hydrophobic waxy material results in the lotus effect on glycerin droplet 24, so that the glycerin droplet 24 will not fully penetrate the substrate 12 with the calligraphy paper material immediately.

Figure 4:
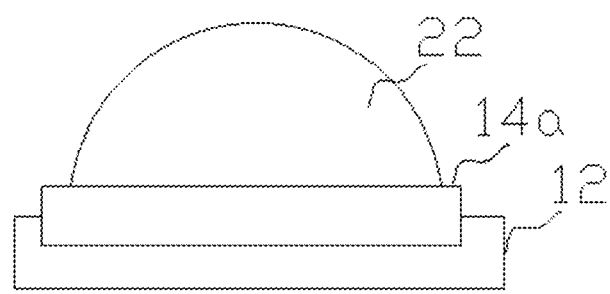
FIG. 4 illustrates a sectional view of a droplet of the liquid to be measured, which is dropping on the biomedical testing sheet of the invention.

Therefore, the hydrophobic property of the waxy material is used to achieve an effect similar to the lotus effect. FIG. 4 illustrates a sectional view of a droplet of the liquid to be measured after being dropped on the biomedical testing sheet of the invention. As shown, the contact angle that the droplet 22 to be measured contacts the surface of the carrying unit 14a with the waxy material shows that the hydrophobic waxy material results in an effect similar to the lotus effect on the biomedical testing sheet. Thus, the time required for droplet 22 to penetrate substrate 12 completely can be increased. Meanwhile, when the droplets to be measured react with the reagent is deposited in the waxy material carrying unit 14a of the biomedical testing sheet of the invention, the combined property of the calligraphy material substrate 12 and the waxy material carrying unit 14a enhance the coloring effect so that the color intensities can be determined easily and accurately.

Figure 5:
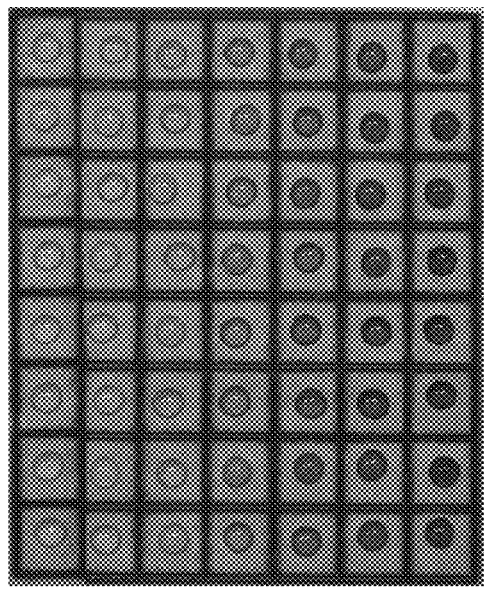
FIG. 5 is a photograph of the biomedical testing sheet with 56 carrying units used in the testing without erasing droplets according to an embodiment of the invention.

FIG. 5 is a photograph of the biomedical testing sheet with 56 carrying units used in the testing without erasing droplets according to an embodiment of the invention. All carrying units are applied in droplets of different concentrations to be measured and then dropped by the reagent. After the reaction of the droplets and the reagent, the droplets on the carrying unit present colors of varying intensity. As shown in the circular portions of FIG. 5, the colors and the intensities of the droplets on the carrying units can be measured without erasing the droplets.

Figure 7:
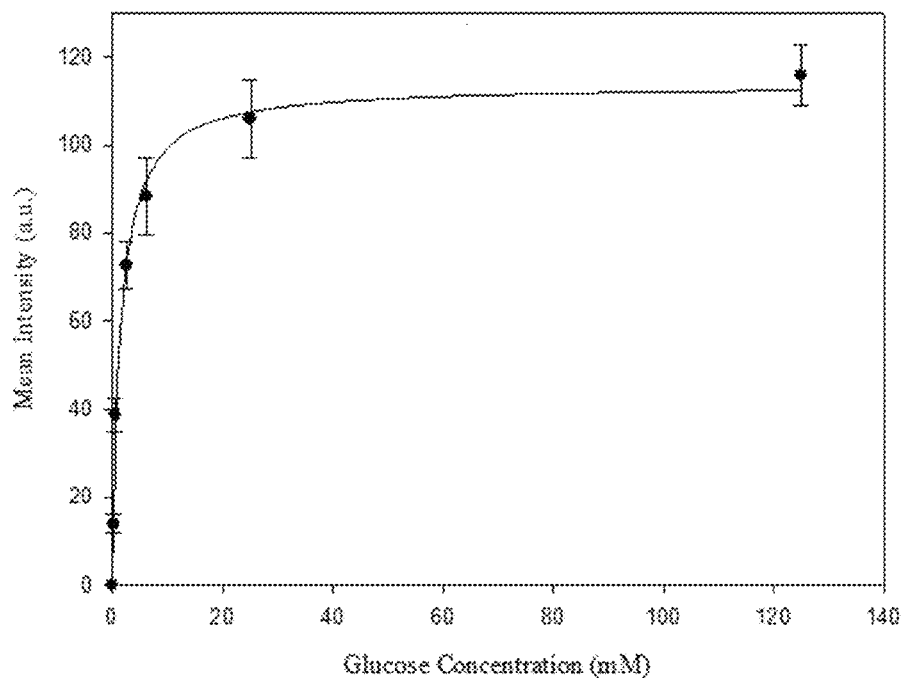
FIG. 7 is a graph illustrating the relationship of the glucose concentrations and the intensities of the droplets when the glucose concentrations are measured.
Figure 9:
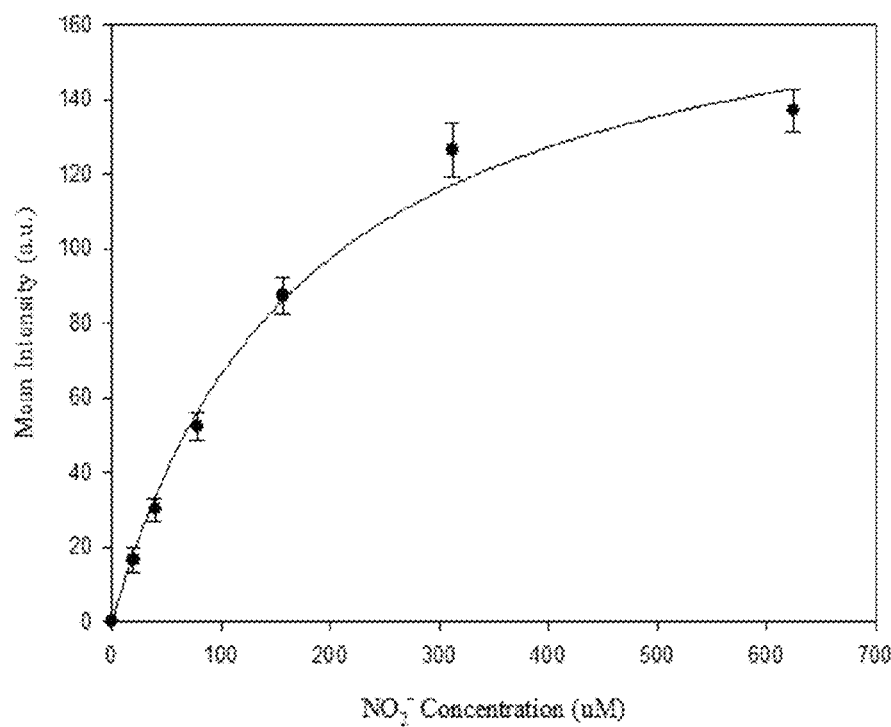
FIG. 9 is a graph illustrating the relationship of the nitrite concentrations and the intensities of the droplets when the nitrite concentrations are measured.

FIG. 7 is a graph illustrating the relationship between glucose concentration and droplet intensity when the glucose concentrations are measured, and FIG. 9 is the graph illustrating the relationship of the nitrite concentrations and the intensities of the droplets when the nitrite concentrations are measured. Both of FIGS. 7 and 9 demonstrate consistent linear relationships that reveal the concentrations of the droplets to be measured based on the intensities of the colors of the droplet traces.

Figure 6:
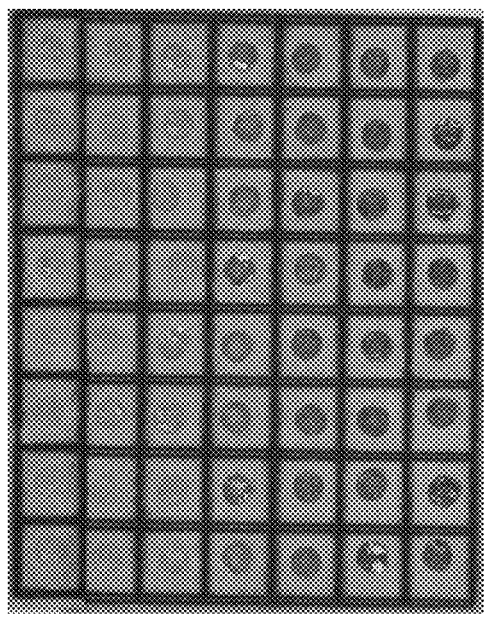
FIG. 6 is a photograph of the biomedical testing sheet with 56 carrying units used in the testing with erasing droplets according to an embodiment of the invention.

FIG. 6 is a photograph of the biomedical testing sheet with 56 carrying elements used in the testing with erasing droplets according to an embodiment of the invention. All carrying units are dropped by droplets with different concentrations to be measured, and then dropped by the reagent. After the reaction of the droplets and the reagent, the droplets on the carrying unit present colors with different intensities. Then, after erasing droplets, the colors and their intensities of traces (circular portions of FIG. 6) left by the droplets on the carrying units are measured.

Figure 8:
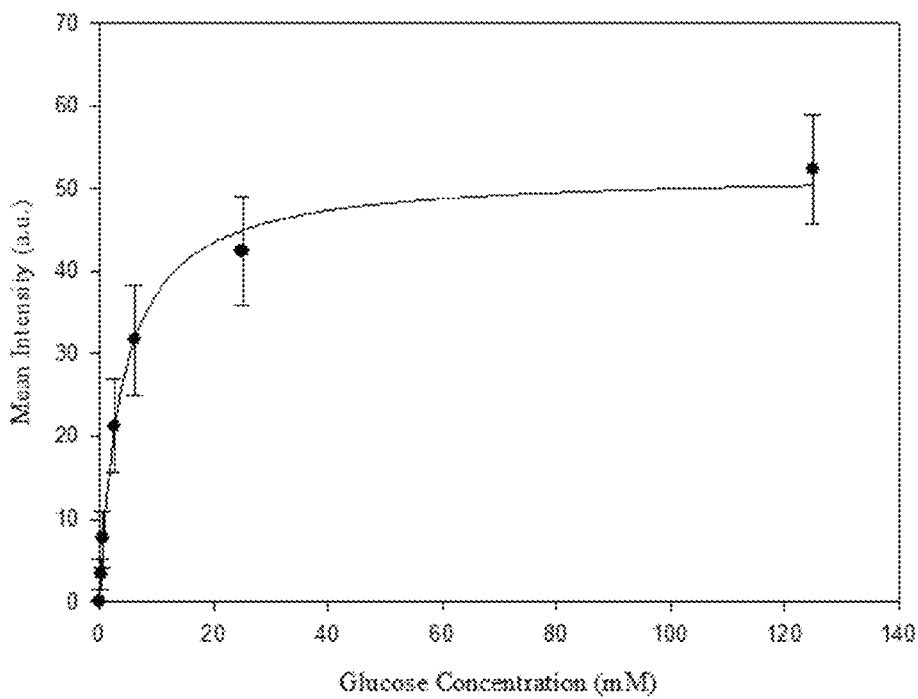
FIG. 8 is a graph illustrating the relationship of the glucose concentrations and the intensities of the droplet traces when the glucose concentrations are measured.
Figure 10:
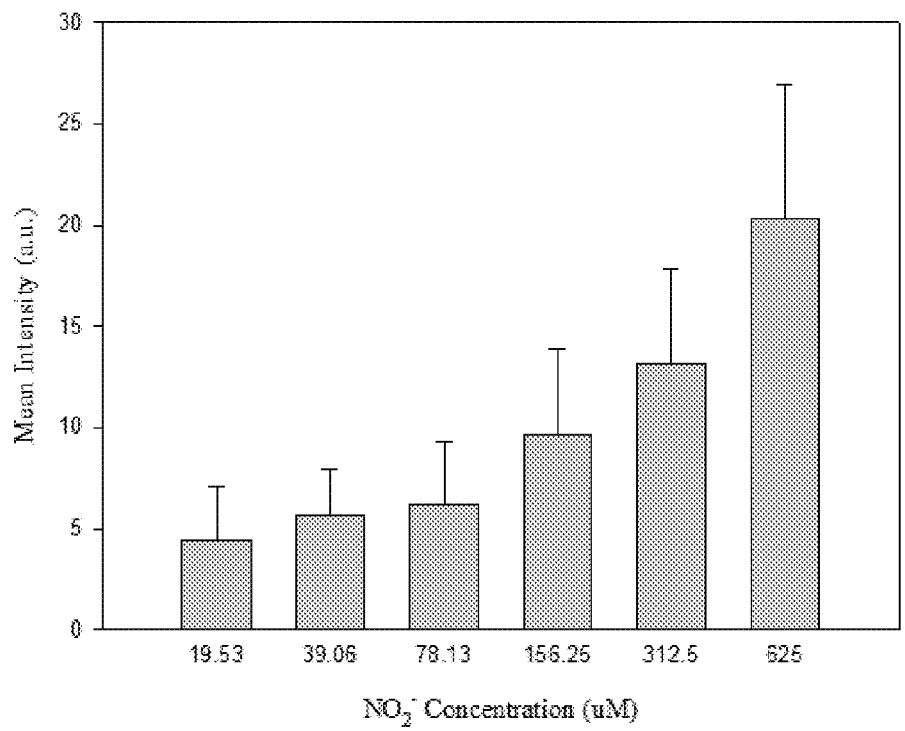
FIG. 10 is a graph illustrating the relationship of the nitrite concentrations and the intensities of the droplet traces when the nitrite concentrations are measured.

FIG. 8 is a graph illustrating the relationship of the glucose concentrations and the intensities of the droplet traces when the glucose concentrations are measured, and FIG. 10 is the graph illustrating the relationship of the nitrite concentrations and the intensities of the droplet traces when the nitrite concentrations are measured. FIGS. 8 and 10 show that the concentrations of the droplets have clear linear relationships with the color intensities of the droplet traces.

The above description was given for purposes of explaining specific details of the preferred embodiments to provide a thorough understanding of the invention. However, it will be apparent to one skilled in the art that specific details are not required in order to practice the invention. Therefore, the foregoing descriptions of specific embodiments of the invention are presented for purposes of illustration and description only and should not be construed in any way to limit the scope of the invention. They are not intended to be exhaustive or to limit the invention to the precise forms disclosed; obviously, many modifications and variations are possible in view of the above teachings. The embodiments were chosen and described in order to best explain the principles of the invention and its practical applications, thereby enabling others skilled in the art to best utilize the invention and various embodiments with various modifications as are suited to the particular use contemplated. It is intended that the following Claims and their equivalents define the scope of the invention.

What is claimed is:

1. A biomedical testing sheet, including:
   a substrate with calligraphy paper material,
   wherein the substrate comprises a wax pattern layer, which is a part of a surface of the substrate that is coated with a waxy material, and penetrated and diffused by the waxy material, and
   the wax pattern layer comprises plural carrying units that are completely diffused with the waxy material and laterally surrounded by the calligraphy paper material with no waxy material diffused thereinto and protrude from the substrate for carrying one or more droplets of liquids to be measured, and
   the calligraphy paper material with no waxy material diffused thereinto separates the carrying units from one another.

2. The biomedical testing sheet of claim 1, wherein the carrying units are rectangular.

3. The biomedical testing sheet of claim 2, wherein the carrying units form a matrix.

4. The biomedical testing sheet of claim 2, wherein the carrying units are separated by a distance.

5. The biomedical testing sheet of claim 2, wherein the carrying units are the same size.

6. The biomedical testing sheet of claim 1, wherein the calligraphy paper material is polyvinyl chloride.

7. The biomedical testing sheet of claim 1, wherein the carrying units have an upper portion protruding from a top surface of the substrate and a lower portion extending into the substrate and spaced from a bottom surface of the substrate.

8. The biomedical testing sheet of claim 7, wherein the upper portion is made of the waxy material, and the lower portion is made of a combination of the waxy material and the calligraphy paper material.

9. A method for manufacturing a biomedical testing sheet, comprising steps of:
   coating a waxy material on a surface of a substrate, wherein the substrate is calligraphy paper material;
   heat treating the waxy material to make the waxy material penetrate the substrate to form a wax pattern layer, the wax pattern layer formed into plural carrying units that are completely diffused with the waxy material and laterally surrounded by the calligraphy paper material with no waxy material diffused thereinto and protrude from the substrate for carrying one or more droplets of liquids to be measured, wherein the calligraphy paper material with no waxy material diffused thereinto separates the carrying units from one another.

10. The method of claim 9, wherein the carrying units are rectangular.

11. The method of claim 10, wherein the carrying units are formed into a matrix.

12. The method of claim 11, wherein the carrying units are formed separated by a distance.

13. The method of claim 9, wherein the carrying units have an upper portion protruding from a top surface of the substrate and a lower portion extending into the substrate and spaced from a bottom surface of the substrate.

14. The method of claim 13, wherein the upper portion is made of the waxy material, and the lower portion is made of a combination of the waxy material and the calligraphy paper material.

* * * * *